US007272234B2

(12) United States Patent
Sommerfeldt et al.

(10) Patent No.: US 7,272,234 B2
(45) Date of Patent: Sep. 18, 2007

(54) MULTI-CHANNEL ACTIVE CONTROL SYSTEM AND METHOD FOR THE REDUCTION OF TONAL NOISE FROM AN AXIAL FAN

(75) Inventors: Scott D. Sommerfeldt, Mapleton, UT (US); Kent L. Gee, State College, PA (US)

(73) Assignee: Brigham Young University, Provo, UT (US)

( * ) Notice: Subject to any disclaimer, the term of this patent is extended or adjusted under 35 U.S.C. 154(b) by 644 days.

(21) Appl. No.: 10/407,915

(22) Filed: Apr. 4, 2003

(65) Prior Publication Data

US 2003/0219132 A1 Nov. 27, 2003

Related U.S. Application Data

(60) Provisional application No. 60/369,963, filed on Apr. 4, 2002.

(51) Int. Cl.
*A61F 11/06* (2006.01)
*G10K 11/16* (2006.01)
*H03B 29/00* (2006.01)

(52) U.S. Cl. ................. 381/71.11; 381/71.1; 381/71.7; 381/71.8; 381/71.14

(58) Field of Classification Search ............... 381/71.1, 381/71.2, 71.3, 71.7, 71.8, 71.9, 71.11, 71.14
See application file for complete search history.

(56) References Cited

U.S. PATENT DOCUMENTS 4,412,445 A * 11/1983 Spellicy ..................... 73/24.02
5,343,713 A * 9/1994 Okabe et al. ................. 62/296
5,448,645 A 9/1995 Guerci
5,966,452 A 10/1999 Norris
6,188,770 B1 2/2001 Okada

OTHER PUBLICATIONS

Nelson, et al., The Minimum Power Output of Free Field Point Sources and the Active Control of Sound, Journal of Sound and Vibration (1987) 116(3), pp. 397-414.
Koopmann, et al., Active Source Cancellation of the Blade Tone Fundamental and Harmonics in Centrifugal Fans, Journal of Sound and Vibration (1988) 126(2), pp. 209-220.
Lauchle, et al., Active Control of Axial-flow Fan Noise, Acoustical Society of America vol. 101, No. 1, Jan. 1997, pp. 341-349.
Mei Q. Wu, Active Cancellation of Small Cooling Fan Noise From Office Equipment, inter-noise, Jul. 10-12, 1995, pp. 525-528.
D.A. Quinlan, Application of Active Control to Axial Flow Fans, Acoustics Research Department, AT&T Bell Laboratories, Oct. 1992, pp. 92-101.
Carl H. Gerhold, Active Control of Fan-Generated Tone Noise, NASA Langley Research Center, AIAA Journal vol. 35, No. 1, Jan. 1997, pp. 17-22.
Thomas, et al., Active Control of Fan Noise from a Turbofan Engine, Virginia Polytechnic Institute and State University, AIAA Journal vol. 32, No. 1, Jan. 1994, pp. 23-30.

* cited by examiner

*Primary Examiner*—Vivian Chin
*Assistant Examiner*—Douglas Suthers
(74) *Attorney, Agent, or Firm*—Thorpe North & Western LLP

(57) ABSTRACT

A multi-channel active noise control system and method of reducing tonal noise emanating from a tonal noise source are disclosed. The system may include an adaptive controller, a plurality of loudspeakers driven by the loudspeaker, one or more microphones for generating one or more error signals to feedback to the adaptive controller and optionally a reference signal source to provide the adaptive controller with frequency information associated with the tonal noise source. The system and method of the present invention are applicable to any tonal noise source, including but not limited to axial fans.

17 Claims, 9 Drawing Sheets

MULTI-CHANNEL ACTIVE CONTROL SYSTEM AND METHOD FOR THE REDUCTION OF TONAL NOISE FROM AN AXIAL FAN

CROSS-REFERENCE TO RELATED APPLICATION

This patent application claims benefit of, and priority to, U.S. provisional patent application Ser. No. 60/369,963, filed Apr. 4, 2002, titled: "A Multi-channel Active Control System for the Reduction of Tonal Noise from an Axial Fan," the contents of which are expressly incorporated herein by reference for all purposes.

BACKGROUND OF THE INVENTION

1. Field of the Invention

The present invention relates generally to active noise suppression. More particularly, this invention relates to a multi-channel active control system and method for the reduction of tonal noise from an axial fan.

2. Related Art

Axial fans are air-moving devices in which the air flows parallel to the axis of rotation. One common use of these fans is in the cooling of electronic equipment, such as computers, copiers, overhead projectors, and related technology, where the fan is most often mounted on one face of the equipment enclosure. The noise generated from the fans on these devices can contribute significantly to background noise levels in the workplace, classroom, and anywhere else such fans are located, causing annoyance and disrupting concentration to persons that can hear the noise. The radiated noise is composed of both broadband and tonal components. The tonal components are referred to herein as "tones." The tones may rise as much as 25-30 decibels (dB) above broadband levels, and therefore typically dominate an axial fan's overall spectrum.

The tones most typically present in an axial fan's radiated spectrum are the blade passage frequency (BPF), calculated by multiplying the number of fan blades by the shaft speed in revolutions per second, and several harmonics, i.e., integer multiples of the BPF. The tones are typically caused by obstructions near the inlet or the outlet of the fan, such as fan supports, wires, or finger guards. Because the tones are usually the most dominant and noticeable part of the fan's spectrum, it is therefore desirable to reduce their levels or eliminate them entirely.

Techniques relating to fan noise reduction can be categorized as either passive or active. Passive noise reduction techniques typically use some sort of sound absorbing or muffling device. Whereas active noise reduction techniques typically involve the generation of an acoustic signal through a control source designed to destructively interfere with and therefore reduce the fan's acoustic radiation. Passive techniques have been limited in their effectiveness for two reasons: (1) the tonal content of the fan's radiation is often relatively low in frequency, such that a muffler or absorber would have to be made impractically large to fulfill its purpose and (2) the demand for reduction in size of technology makes the removal of obstructions to the flow of air near the inlet and outlet of the fan difficult. Because of the ineffectiveness of passive noise reduction techniques, conventional approaches disclosed over the past decade have primarily investigated the use of active noise control (ANC) to reduce the tonal noise from axial fans.

ANC has been applied to large fans, such as turbofan engines for commercial aircraft. In these larger turbofans, tonal noise is principally caused by the rotor-stator interaction, see for example, Thomas et al., "Active Control of Fan Noise from a Turbofan Engine," AIAA JOURNAL, Vol. 32, No. 1, pp. 23-30, January 1994. Thomas et al: disclosed tests on an executive jet-type turbofan engine with a ring of actuators surrounding the fan. The error sensors were located in the far field outside the engine duct. Some limited on-axis far field control was achieved. Carl H. Gerhold, "Active Control of Fan-Generated Tone Noise," AIAA JOURNALm, Vol. 35, No. 1, pp. 17-22, January 1997, discloses in-duct error sensors in order to improve on the effort by Thomas et al. with a ducted fan meant to simulate an engine environment. Gerhold disclosed that the new sensor location helped reduce acoustic spillover (increases in pressure levels) at large angles relative to the duct's axis, increasing the potential for obtaining global control of fan tones.

ANC has also been applied to a centrifugal fan or blower, such as those used in HVAC systems, see for example, Koopmann et al. "Active Source Cancellation of the Blade Tone Fundamental and Harmonics in Centrifugal Fans," JOURNAL OF SOUND AND VIBRATION, 126(2) pp. 209-220, 1988. Koopmann et al. achieved duct inlet and outlet noise reduction for a fan's first two harmonics of a ducted centrifugal fan having two control sources located within one-quarter wavelength of the aerodynamic source.

D. A. Quinlan, "Application of Active Control to Axial Flow Fans", NOISE CONTROL ENGINEERING JOURNAL, Vol. 39, No. 3, pp. 95-101, November-December, 1992, discloses a single channel control system in a research setting. The Quinlan apparatus included a single loudspeaker and error microphone. Since then, several variations of this single channel system have been proposed and investigated, see for example, Lauchle et al., "Active Control of Axial-flow Fan Noise," JOURNAL OF THE ACOUSTICAL SOCIETY OF AMERICA, 101 (1), pp. 341-49 (1997); Wu, "Active Cancellation of Small Cooling Fan Noise from Office Equipment," PROCEEDINGS OF INTER-NOISE 95, Newport Beach, Calif. (Noise Control Foundation, Poughkeepsie, N.Y., 1995), pp. 525-28; U.S. Pat. No. 6,188,770 B1 to Okada and U.S. Pat. No. 5,448,645 to Guerci. There are several deficiencies with the above conventional approaches that make wide-scale implementation of the proposed systems both unsuitable and impractical.

First, the single channel systems disclosed in Quinlan, Lauchle et al. and Wu demonstrate an inability to significantly attenuate on a global scale more than the BPF and second harmonic, whereas, higher harmonics are often present and their reduction desirable. Second, Lauchle et al. and Wu disclose error microphones placed in the fan's acoustic near-field, a virtual necessity in a practical implementation of such a control system, where the error sensor used would have to be located in or on the equipment enclosure. However, there is no evidence that the methods disclosed in Lauchle et al. and Wu for determining the appropriate near-field microphone locations could ever be implemented on a wide-scale basis.

Okada discloses a system similar to Quinlan, though there are several variations on nonacoustic sensors disclosed. Like the other single channel systems disclosed, the limitations of Okada's system include: (1) only a single actuator and microphone are used, which is insufficient for higher harmonics of the BPF, (2) the diagram (FIG. 7 of Okada) of the adaptive system described shows the orientation of the loudspeaker along a plane parallel to the axis of the fan, which could provide a mismatch in the sources' directivities at higher harmonics and, (3) there is no indication of the error microphone being placed in the acoustic near-field of the fan, nor is there any mention made of how the microphone placement will result in global attenuations of the fan's BPF and its harmonics.

Guerci exhibits fundamental physical inconsistencies, which would likely limit the system's ability ot globally attenuate a fan's BPF over extended periods of time. Guerci intended to eliminate the need for a digitally-based adaptive controller by using a microphone and a band pass filter to sense the frequency to be cancelled and then manually adjusting the amplitude and phasing of an array of control loudspeakers to attenuate the tone. There are differences of varialbe speed fans, there is no provision for the variations in amplitude and phase of the fan's radiation due to changes of loading on the fan over time.

The Guerci system requires constant readjustment for changes in amplitude and phase. In addition, the amplitude of the fan noise will vary as a function of frequency. There is no provision made in Guerci for adjusting loudspeaker amplitudes at different fan speeds. Furthermore, Guerci's band pass filter, which extracts the harmonic noise from the microphone's signal, has a center frequency equal to the fan's BPF that is manually adjusted with a potentiometer. With fluctuations in the fan's BPF due to airflow changes, the filter's center frequency would have to be frequently readjusted. Finally, there is no provision for dealing with harmonics of the BPF, which are often noticeable to the observer, even when the fundamental has been attenuated. Accordingly, there exists a need in the art for a multi-channel active control system and method for the reduction of tonal noise from axial fans.

SUMMARY OF THE INVENTION

A multi-channel active noise control system according to the present invention is disclosed. The multi-channel active noise control system may include loudspeakers arranged relative to a tonal noise source and at least one microphone for generating at least one error signal. The multi-channel active noise control system may include an adaptive controller coupled to the loudspeakers and the at least one microphone, wherein the adaptive controller drives each of the loudspeakers with amplitudes and phases selected to minimize radiated acoustic power in response to the at least one error signal.

A method of reducing tonal noise emanating from a tonal noise source is also disclosed. The method may include selectively arranging loudspeakers around the tonal noise source, and placing a plurality of microphones within an extreme near-field of the loudspeakers and the tonal noise source. The method may further include driving amplitude and phase of each of the loudspeakers in response to signals generated by the plurality of microphones to reduce the tonal noise emanating from the tonal noise source.

Additional features and advantages of the invention will be apparent from the detailed description which follows, taken in conjunction with the accompanying drawings, which together illustrate, by way of example, features of the invention.

BRIEF DESCRIPTION OF THE DRAWINGS

The following drawings illustrate exemplary embodiments for carrying out the invention. Like reference numerals refer to like parts in different views or embodiments of the present invention in the drawings.

DETAILED DESCRIPTION

Figure 1:
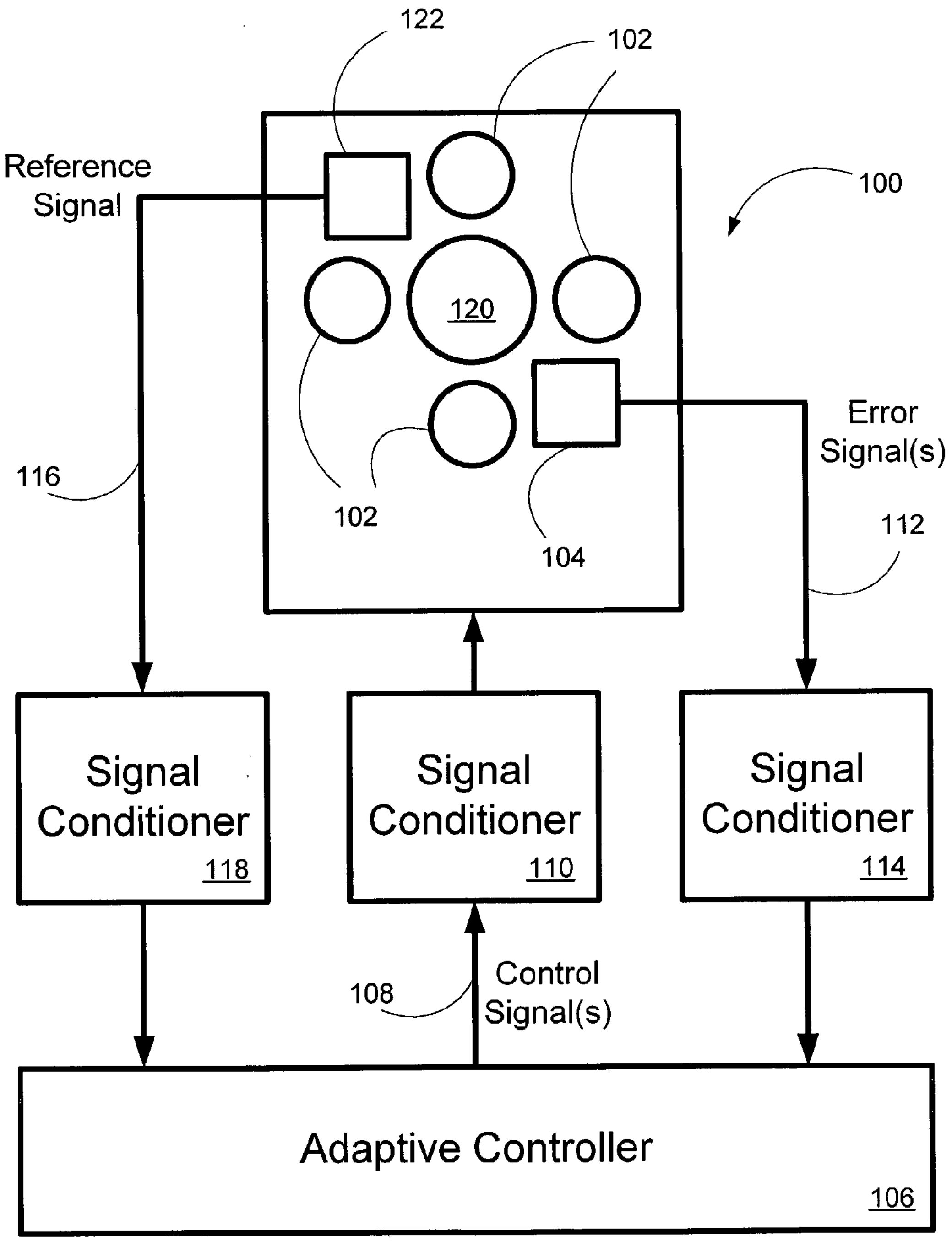
FIG. 1 illustrates a block diagram of a multi-channel active noise control system for reducing noise from an axial fan according to the present invention.

A multi-channel active noise control system and method of reducing tonal noise emanating from a tonal noise source are disclosed. The system and method of the present invention are applicable to any tonal noise source, including, but not limited to, axial fans. The present invention, in one or more of the disclosed embodiments, overcomes deficiencies existent in conventional approaches to reducing tonal noise in axial fans. The present invention achieves significant global attenuation of the tonal noise radiated from an axial-flow fan (hereinafter "axial fan"). Furthermore, the present invention provides a practical implementation with all control sources and sensors located closely to the axial fan. For ease of discussion, an axial fan is the exemplary tonal noise source discussed in the various embodiments of the present invention.

In a presently preferred embodiment of the present invention, the capability to globally attenuate as many as five harmonics of the BPF by as much as 19 dB has been demonstrated. In another aspect of the present invention, a theoretical analysis has been performed and experimentally verified showing that there are predictable near-field locations that consistently result in global reductions of the unwanted tonal noise. The present invention employs an adaptive controller to adjust for changes in frequency, amplitude and phase.

Reference will now be made to exemplary embodiments illustrated in the drawings and specific language will be used herein to describe the same. It will nevertheless be understood that no limitation of the scope of the invention is thereby intended. Alterations and further modifications of the inventive features illustrated herein and additional applications of the principles of the inventions as illustrated herein, which would occur to one skilled in the relevant art and having possession of this disclosure, are to be considered within the scope of the invention.

FIG. 1 illustrates a block diagram of a multi-channel active noise control system 100 for reducing noise from an axial fan 120 according to the present invention. The multi-channel active noise control system 100 may include loudspeakers 102 (four loudspeakers are shown in FIG. 1), at least one microphone 104 and an adaptive controller 106 coupled to the loudspeakers 102 and microphone 104. For convenience of discussing FIG. 1, reference will be made to one microphone 104. However, other embodiments of the present invention may include more than one microphone 104. The multi-channel active noise control system 100 may also include an optional nonacoustic reference sensor 122 for feed-forward embodiments of the present invention.

The loudspeakers 102 may be driven by control signals 108 from the adaptive controller 106. Generation of the control signals 108 is more fully described below. A signal conditioner 110 may be used to convert from digital-to-analog conversion, filter and amplify the control signals 108. Signal conditioner 110 may include digital-to-analog conversion, filtering and amplification functions. The functionality provided by signal conditioner 110 may be achieved in a variety of ways known to one of ordinary skill in the art, for example, by using discrete electronic components, as a block of components like the signal conditioner 110 illustrated in FIG. 1, or as components combined with the functionality of adaptive controller 106.

The loudspeakers 102 are preferably mounted in an array around the fan at equal angles around, at equal radii from, and coplanar with, the axial fan 120. The present invention may be configured with any number of loudspeakers 102. For example, a presently preferred embodiment of a multi-channel active noise control system 100 includes four loudspeakers 102 configured at 90-degree angles relative to each other and at equal radii from and coplanar with the axial fan 120. The loudspeakers 102 are preferably placed in as close proximity to the fan as is reasonable, in order to increase the acoustic coupling between the speakers and the fan.

Microphone 104 may generate an error signal 112 as more fully described below. Signal conditioner 114 may be used to filter, amplify (if necessary) and convert from analog-to-digital the error signal 112. Signal conditioner 114 may include electrical circuits for filtering, amplification and analog-to-digital conversion. The functionality provided by signal conditioner 114 may be achieved in a variety of ways known to one of ordinary skill in the art, for example, by using discrete electronic components, as a block of components like the signal conditioner 114 illustrated in FIG. 1, or as components combined with the functionality of adaptive controller 106. The microphone 104 is positioned along or near the theoretical nodes, as described below and is coplanar with the fan and loudspeakers, or very nearly so, relative to the wavelengths of the frequencies of interest.

The placement of microphone 104 relative to loudspeakers 102 and axial fan 120 is selected such that the microphone is located at a near-field pressure node of a spatial pressure plot corresponding to a condition of minimized acoustic power radiation. See related discussion regarding microphone placement below.

Figure 5:
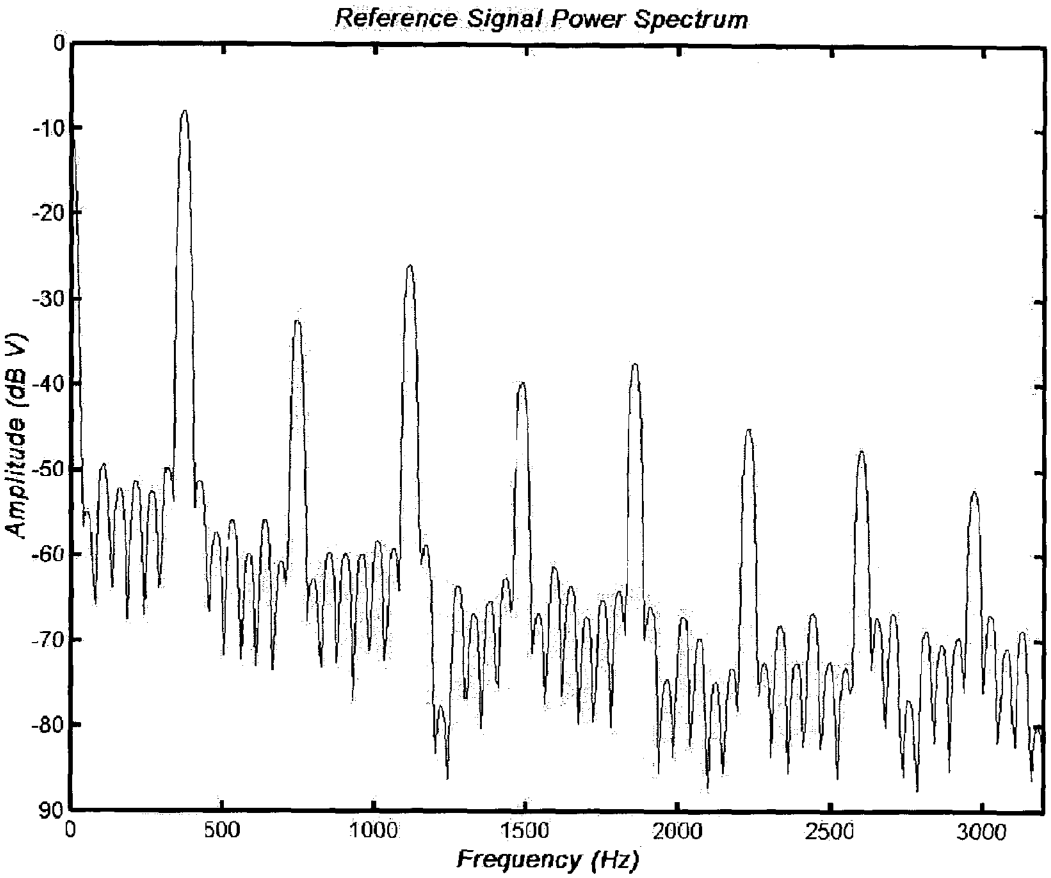
FIG. 5 illustrates a graph of a representative reference signal obtained directly from a reference sensor according to the present invention.
Figure 6:
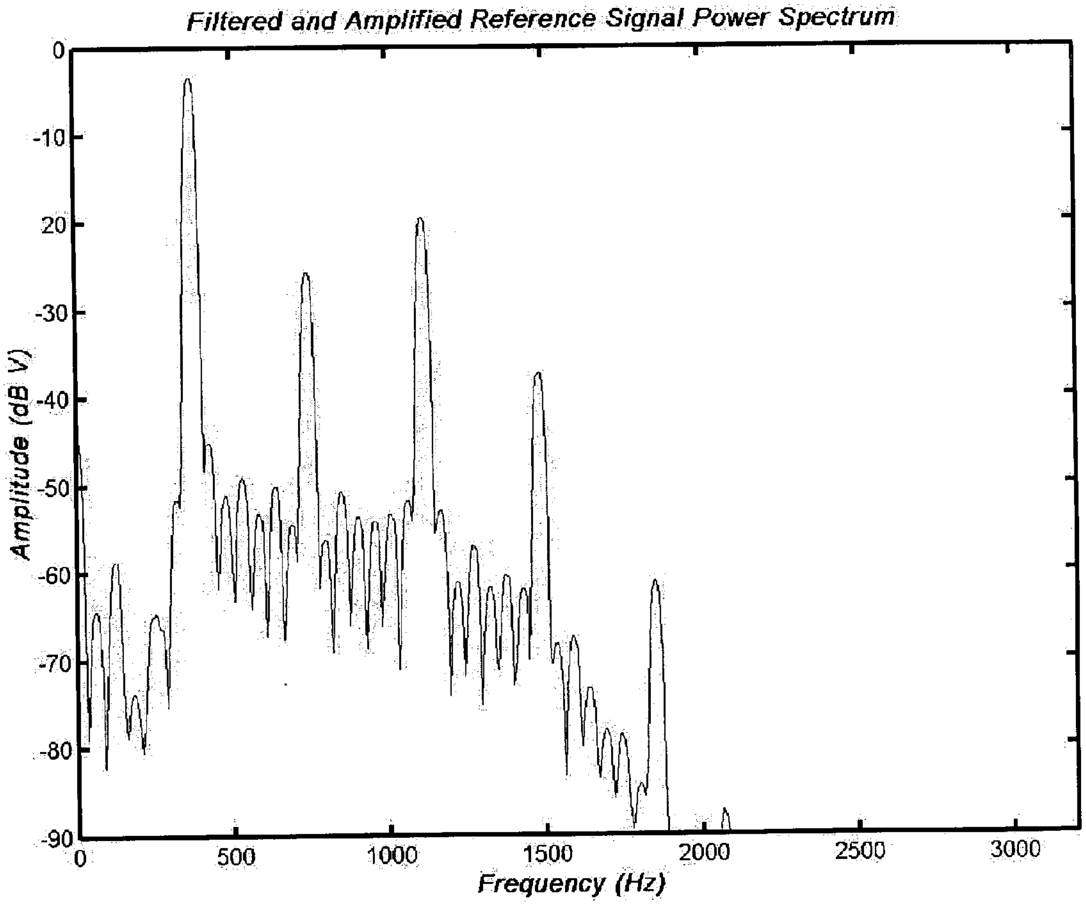
FIG. 6 illustrates a graph of the representative reference signal 116 after filtering according to the present invention.

The nonacoustic reference sensor 122 may be used to generate a reference signal 116 as more fully described below. The nonacoustic reference sensor 122 may be an infrared emitter/detector pair located on opposite sides of fan blades associated with the axial fans. The optional nonacoustic reference sensor 122 may be filtered, amplified and converted from analog-to-digital by a signal conditioner 118. Signal conditioner 118 may include electrical circuits for filtering, amplification and analog-to-digital conversion. An example of this filtering is shown in FIGS. 5 and 6. FIG. 5 illustrates a graph of a representative reference signal 116 obtained directly from a reference sensor 106 according to the present invention. FIG. 6 illustrates a graph of the representative reference signal 116 after filtering according to the present invention.

The functionality provided by signal conditioner 118 may be achieved in a variety of ways known to one of ordinary skill in the art, for example, by using discrete electronic components, as a block of components like the signal conditioner 110 illustrated in FIG. 1, or as components combined with the functionality of adaptive controller 106. The nonacoustic reference sensor 122 may be configured to generate a reference signal 116 having a frequency related to the tonal noise to be reduced by the multi-channel active noise control system 100. Reference signal 116 is related to the BPF associated with the axial fan 120.

The adaptive controller 106 is configured for connection to the loudspeakers 102, one or more microphones 104 and the nonacoustic reference sensor 122. The adaptive controller 106 drives each of the loudspeakers 102 independently. The adaptive controller 106 drives each loudspeaker's amplitude and phase in order to minimize radiated acoustic power in response to the error signal 112 from the microphone 104. Of course, where a plurality of microphones 104 are used, the adaptive controller 106 may drive each of the loudspeakers in response to a plurality of error signals 112. The adaptive controller 106 is configured to generate new control signals 108, based on the error signals 112, and the process repeats itself such that the error is eventually minimized and continually kept at or near that minimum. The adaptive controller 106 may include a multi-channel filtered-x LMS algorithm.

Figure 2:
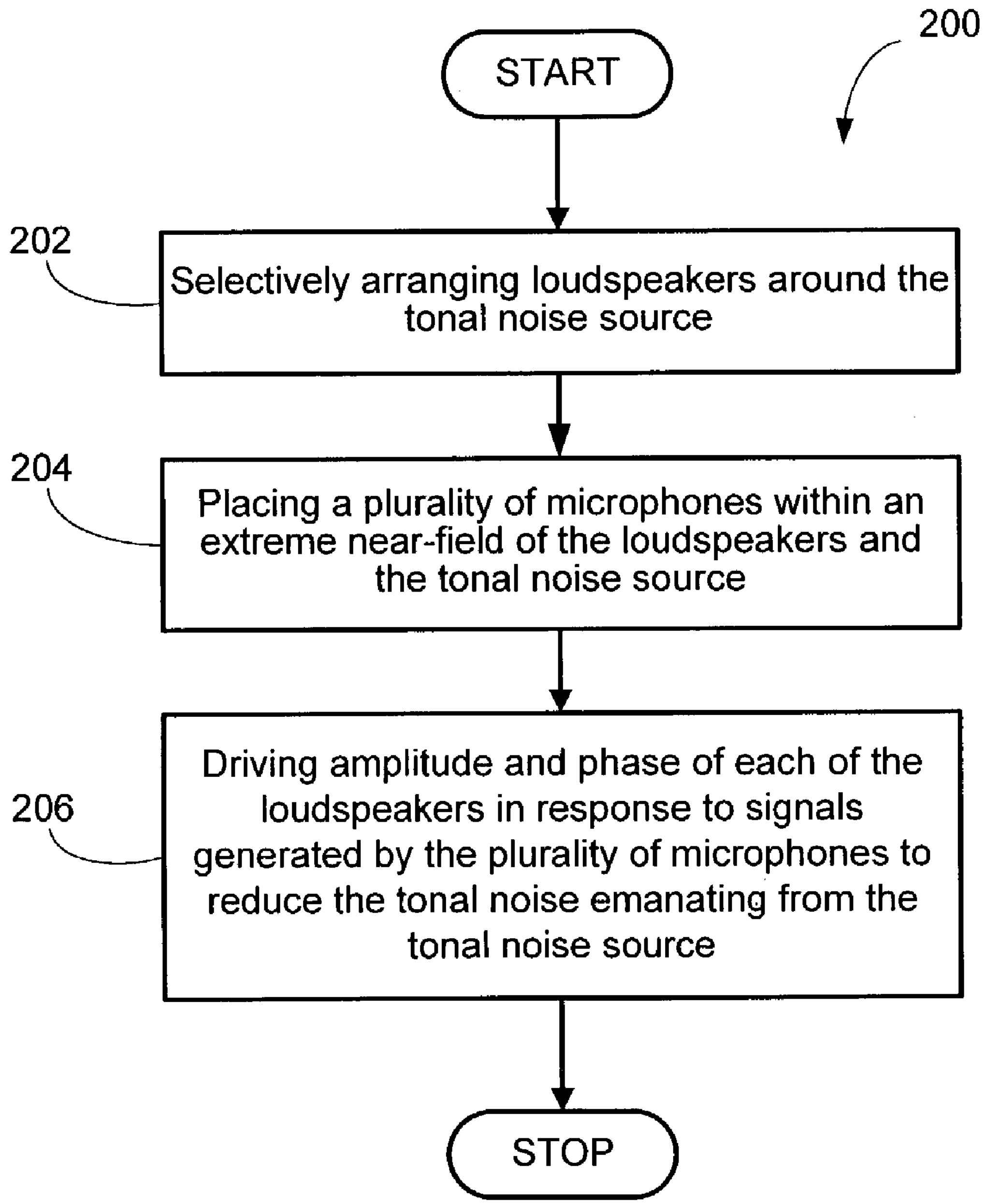
FIG. 2 is a flow chart of an embodiment of a method of reducing tonal noise emanating from a tonal noise source according to the present invention.

FIG. 2 is a flow chart of an embodiment of a method 200 of reducing tonal noise emanating from a tonal noise source in accordance with the present invention. Method 200 may include arranging 202 loudspeakers around the tonal noise source and placing 204 a plurality of microphones within an extreme near-field of the loudspeakers and the tonal noise source. Arranging 202 the loudspeakers around the tonal noise source may include placing each of the loudspeakers coplanar with, and at equal angles and radii around, a center of the tonal noise source. Method 200 may further include driving 206 amplitude and phase of each of the loudspeakers in response to signals generated by the plurality of microphones to reduce the tonal noise emanating from the tonal noise source. Method 200 may also include obtaining a frequency associated with the tonal noise emanating from the tonal noise source. As noted above, the tonal noise for an axial fan includes the BPF and associated harmonics. A nonacoustic sensor may be used to measure the BPF and associated harmonics for input to an adaptive controller.

Placing 204 a plurality of microphones within an extreme near-field of the loudspeakers and the tonal noise source may include modeling each of the loudspeakers and the axial fan as point source monopoles and deriving an expression for radiated power based on the modeling. Placing 204 may further include calculating amplitudes and phases of each of the loudspeakers to minimize the expression for radiated power and plotting spatial pressure in the plane containing the loudspeakers and the tonal noise source. Placing 204 may also include determining near-field pressure nodes corresponding to a condition where the radiated power is minimized and placing the plurality of microphones at the near-field pressure nodes.

With regard to modeling, the terms “loudspeaker,” “secondary source” and “control source” are used synonymously herein. Similarly, with regard to modeling, the terms "axial fan" and "primary source" are used synonymously herein. The desired number of control sources may be determined by modeling the axial fan and the control sources as point sources. The purpose of this approach is to determine the minimum power radiated by a given loudspeaker configuration. By examining various loudspeaker arrangements and the theoretical attenuation possible for a given arrangement, the desired configuration can then be determined. The control source strength optimization procedure may be summarized as follows. First, control source locations are determined and the control sources are given arbitrary complex strengths relative to the primary source. Second, a mathematical expression for the radiated power from all sources may then be obtained. Third, the source strengths which minimize the total radiated audio power may be obtained by differentiating with respect to the real and imaginary parts of each of the source strengths, setting each resultant equation equal to zero, and solving for the optimal strengths.

Figure 3:
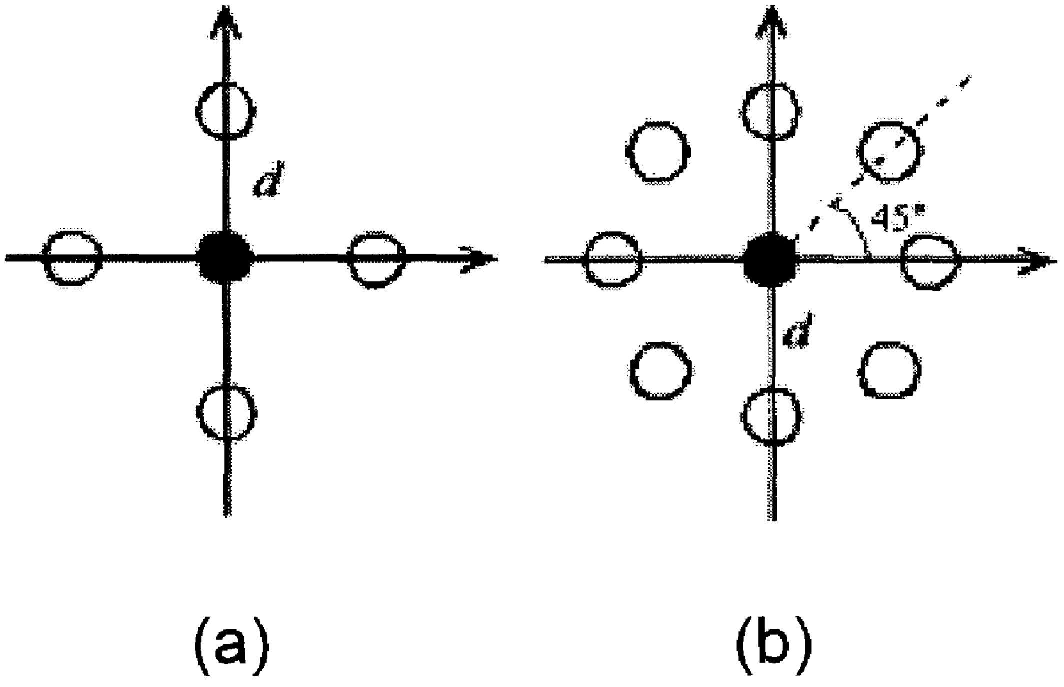
FIG. 3 graphically illustrates two point source monopole configurations used to model the loudspeakers and axial fan for determining microphone placement in accordance with the present invention.

The control source strength optimization procedure outlined above has been performed on a number of configurations. For example, FIG. 3 illustrates a four secondary source arrangement, configuration (a), and an eight secondary source arrangement, configuration (b). For each configuration, the primary source is shaded and located at the origin. For each configuration, the secondary sources are arranged symmetrically around and in the same plane as the primary source.

Figure 4:
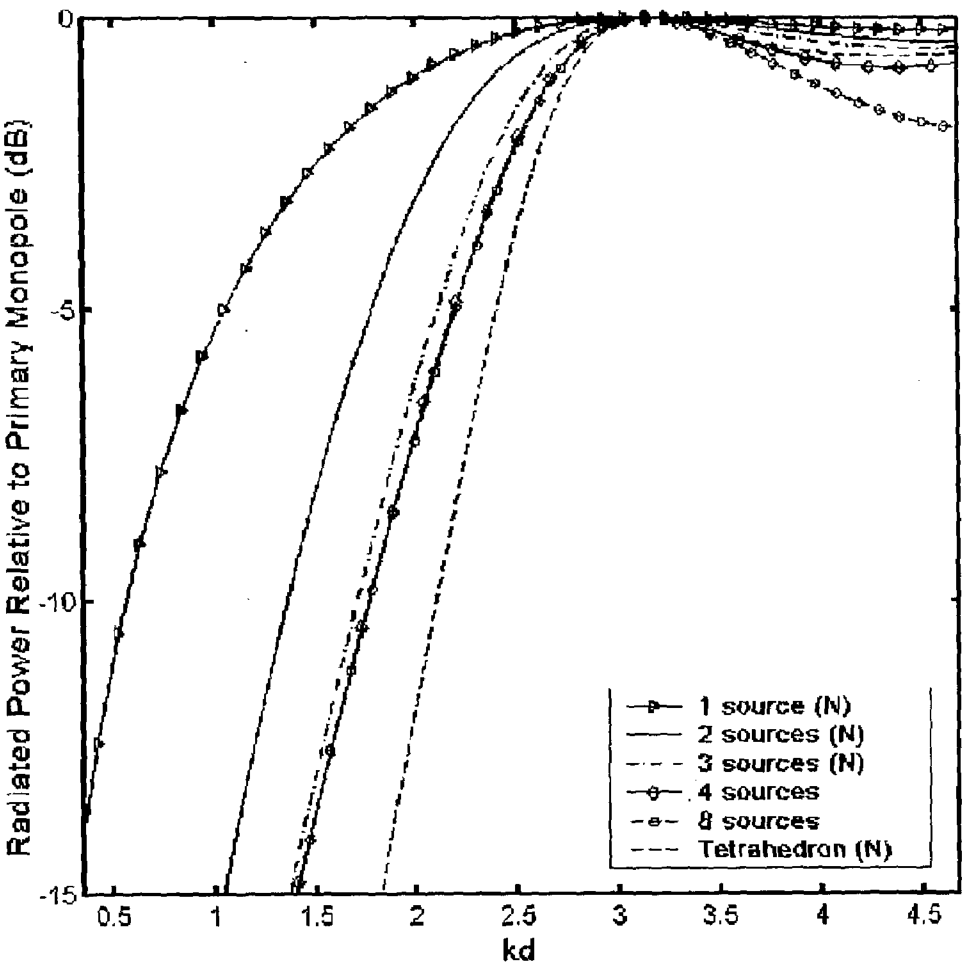
FIG. 4 is a graph of radiated power from loudspeaker configurations relative to an axial fan according to the present invention.

The radiated power relative to the primary source is illustrated in FIG. 4 as a function of "kd," which is the non-dimensionalized separation distance between the primary and secondary sources. Nelson et al. "Active Control of Sound," Academic Press, London, pp. 231-271, 1992 discloses radiated power of various secondary source configurations relative to a primary source, the contents of which are herein incorporated by reference for all purposes. FIG. 4 includes curves for the configurations analyzed previously by Nelson et al. as denoted by (N) in the figure legend, as well as for the secondary source arrangements illustrated in FIG. 3.

An examination of the five source configurations in which all of the secondary sources are coplanar with the axial fan indicates that the additional reduction that can be achieved as more secondary sources are added and symmetry is maintained rapidly lessens. In other words, as kd becomes small, three, four, and eight symmetrically arranged and optimized secondary sources provide essentially the same noise power reduction. While the greatest difference between the three and four secondary source arrangements for $kd<\pi$ is on the order of 1 dB, the largest difference between four and eight sources over the same range is less than 0.2 dB. The power-minimization results for the planar configurations described suggest that either three or four monopole-like actuators (loudspeakers) placed symmetrically around the axial fan are a practical limit to optimize global noise control of a baffled compact primary source (axial fan).

The placement of one or more microphones according to the present invention is determined by an analytical analysis. The fan and each loudspeaker for a given control configuration are modeled as point source monopoles with the loudspeakers possessing an arbitrary amplitude and phase relative to those of the axial fan. From the derived expression for radiated power for a given configuration, the optimal amplitudes and phases of the point sources representing the loudspeakers may be calculated, as described previously, such that the power radiated is minimized. Plotting the spatial pressure in the plane containing the fan and loudspeakers, with each source operating in its minimized-power state, yields certain regions or "nodes," where the radiation is minimal. It has been determined that if the error microphones are placed along or in the vicinity of, relative to a wavelength, where these nodes have been determined by the model and if the tonal noise is driven to a minimum at those locations by the controller, the multi-channel active noise control system 100 will yield significant global reductions of the tonal noise emanating from the axial fan. This includes placement of the microphones along the nodes in the extreme near-field of the fan and loudspeakers.

The adaptive controller 106 may include a digitally-based adaptive algorithm. This adaptive algorithm can be either feedback or feedforward in its configuration. If tonal noise is being targeted, an adaptive feedforward configuration would be the presently preferred algorithm, as it can generally achieve greater attenuation of tonal signals. If a feedforward control algorithm is used, it is presently preferred that the reference sensor used be a nonacoustic reference sensor 122, in order to eliminate acoustic feedback to the reference sensor. As mentioned above, the reference signal 116 from this nonacoustic reference sensor 122 may be filtered so as to only contain the frequencies to be controlled and passed through an analog-to-digital converter to the adaptive controller 106 using, for example, signal conditioner 118.

Figure 7:
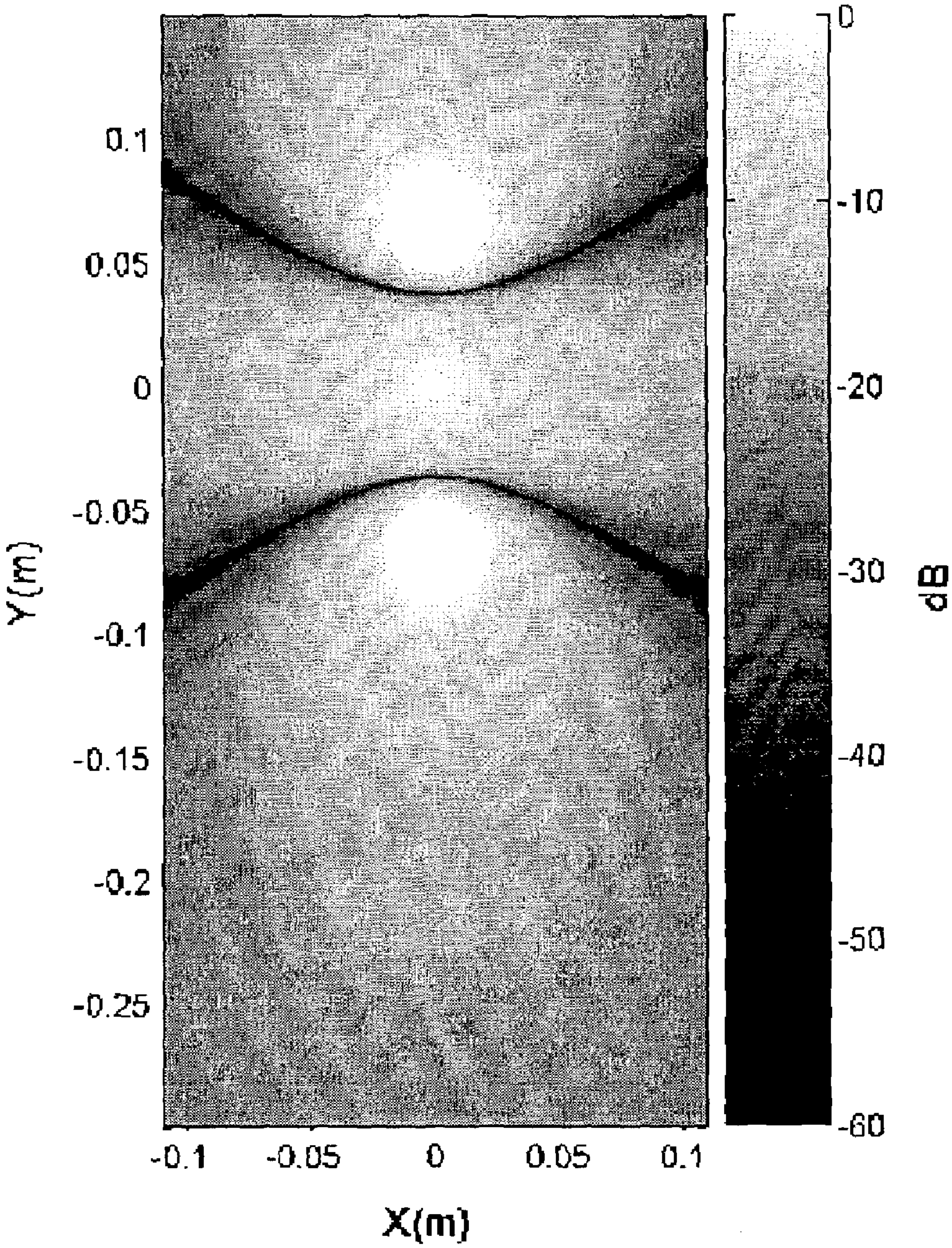
FIG. 7 illustrates a graph of acoustic nodes for a two-loudspeaker/two-microphone (2×2) configuration around an axial fan according to the present invention.
Figure 8:
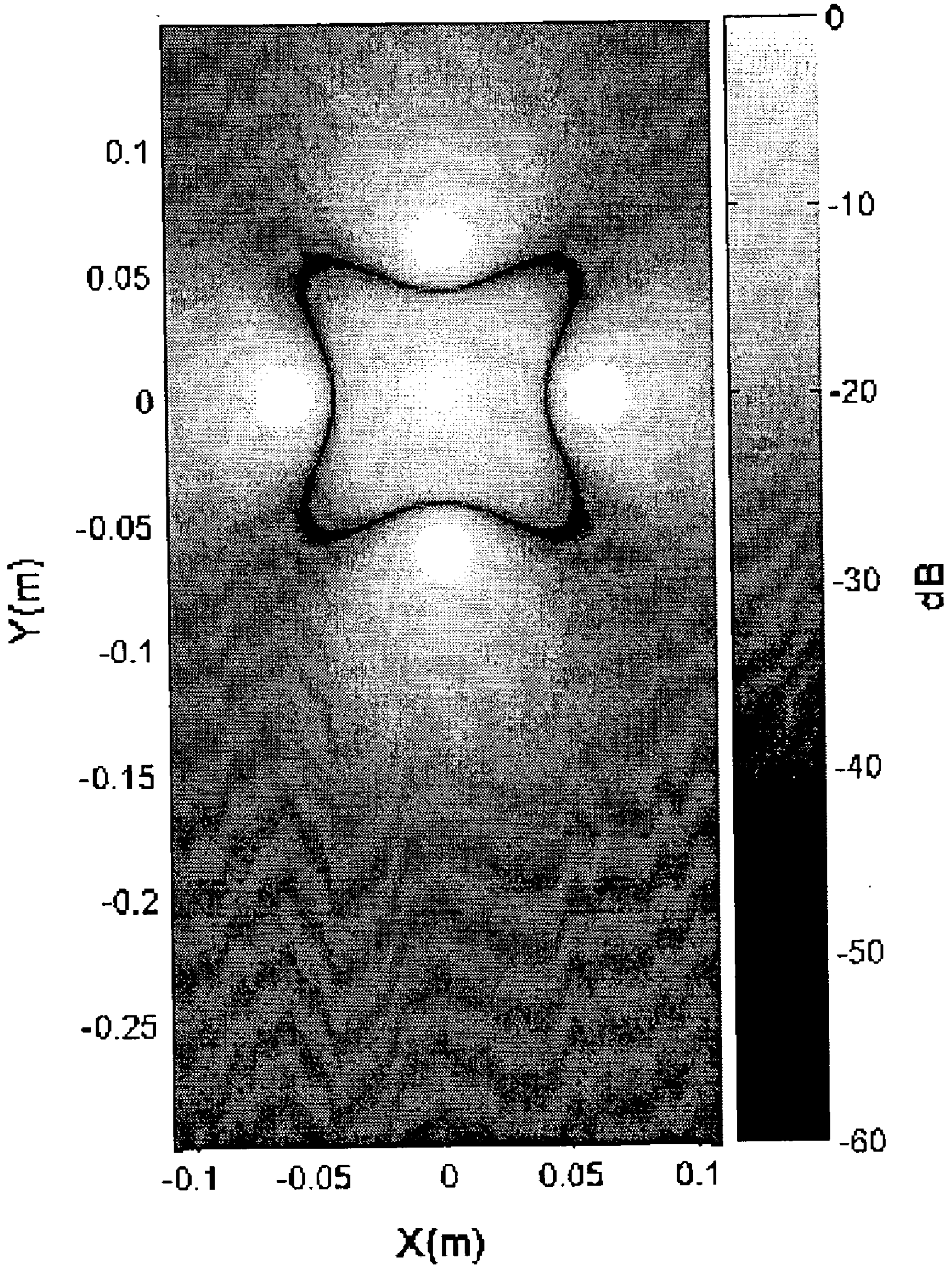
FIG. 8 illustrates a graph of acoustic nodes for a four-loudspeaker/four-microphone (4×4) configuration around an axial fan according to the present invention.

Examples of the control source strength optimization procedure outlined above are shown in FIGS. 7 and 8, which illustrate the near-field regions in which microphones 104 can be ideally located relative to the loudspeakers 102 and the axial fan 120. More specifically, FIG. 7 illustrates a graph of acoustic nodes for a 2×2 configuration around an axial fan 120 where 2×2 signifies that two loudspeakers and two microphones are used. The axial fan 120 is located at the origin (0,0) and the loudspeakers are at coordinates (0, 0.06) and (0, −0.06). The x-axis, y-axis of FIGS. 7 and 8 and all coordinates herein are measured in units of meters. The acoustic nodes are the dark regions where the radiation is significantly lower. FIG. 8 illustrates a graph of acoustic nodes for a 4×4 configuration around an axial fan 120 where 4×4 signifies that four loudspeakers and four microphones are used. Again the axial fan 120 is located at the origin (0,0). The loudspeakers 102 are located at (0.06, 0), (0, −0.06), (−0.06, 0) and (0, 0.06). With the four loudspeakers at equal angles around the fan, the acoustic node forms a closed curve (clover leaf shaped dark region), with ideal locations existing between the fan and speakers and at several locations between adjacent speakers. Those locations between adjacent speakers are normally preferred, as the turbulent wind noise from the fan will be minimized at those locations and yield significant global reductions for the BPF and its harmonics.

Figure 9:
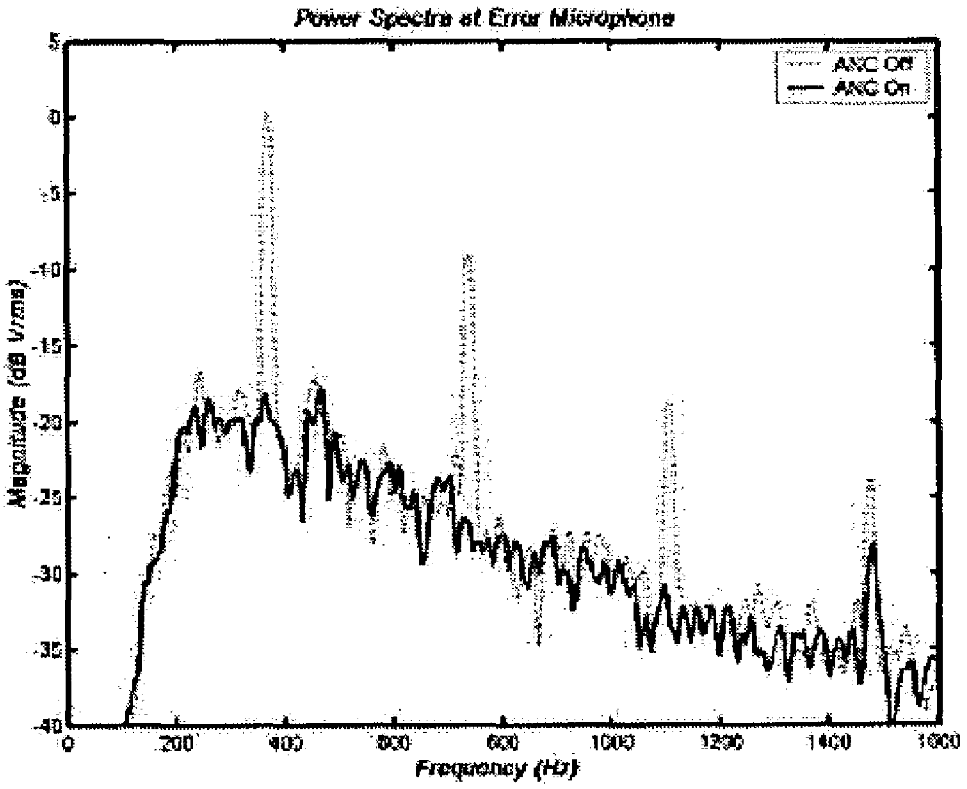
FIG. 9 is a graphical representation of the attenuation results that can be achieved at one of the error sensors when using the 4×4 loudspeaker configuration according to the present invention.

FIG. 9 is a graphical representation of the attenuation results that can be achieved at one of the error sensors when using the 4×4 configuration according to the present invention. The method 200 of the present invention is capable of greatly eliminating the tonal components of the axial fan noise.

Average results obtained for a number of configurations using the system and method of the present invention are shown in Table 1, both for a 2×2 configuration, as well as for a 4×4 configuration. It has been found that arbitrary placement of error microphones in the extreme near field often leads to an unstable controller configuration, whereas placement of the error microphones along the acoustic nodes leads to a stable control configuration and good performance. For the results in Table 1 corresponding to "non-ideal" locations, the results were averaged over non-ideal configurations found to at least be stable. This introduces some bias into the numbers reported here.

TABLE 1

| All results | 370 Hz | | 740 Hz | | 1110 Hz | | 1480 Hz | | A-weighted Total | |
|---|---|---|---|---|---|---|---|---|---|---|
| in dB | MPR | σ | MPR | σ | MPR | σ | MPR | σ | MPR | σ |
| 2 × 2 non-ideal | 5.3 | 2.5 | 10.9 | 5.0 | 6.9 | 3.9 | 4.2 | 2.5 | 6.5 | 2.7 |
| 2 × 2 ideal | 8.4 | 2.5 | 11.9 | 3.1 | 5.9 | 2.7 | 3.1 | 3.0 | 8.0 | 1.2 |
| 4 × 4 non-ideal | 8.2 | 1.6 | 14.9 | 3.4 | 11.0 | 3.9 | 7.4 | 4.1 | 9.5 | 1.5 |
| 4 × 4 ideal | 10.1 | 1.0 | 16.1 | 2.1 | 12.8 | 2.4 | 8.7 | 3.5 | 11.4 | 0.4 |

Table 1 above, shows mean-square pressure reduction (MPR) and standard deviation (σ), in dB, averaged over the eight best trials for each type of configuration. The designation "ideal" signifies the microphones 104 are located along the theoretical nulls or acoustic nodes and the designation "non-ideal" means the microphones 104 are located somewhere off the nulls. Results for the first four harmonics of the BPF and the overall A-weighted tonal levels are shown.

Further details on implementing the multi-channel active noise control system and method of the present invention may be found in Kent L. Gee, "Multi-Channel Active Control of Axial Cooling Fan Noise," Master of Science Thesis, Brigham Young University, Provo, Utah, August 2002, the contents of which are herein incorporated by reference for all purposes.

It is to be understood that the above-referenced arrangements are illustrative of the application for the principles of the present invention. Numerous modifications and alternative arrangements can be devised without departing from the spirit and scope of the present invention while the present invention has been shown in the drawings and described above in connection with the exemplary embodiments of the invention. It will be apparent to those of ordinary skill in the art that numerous modifications can be made without departing from the principles and concepts of the invention as set forth in the claims.

What is claimed is:

1. A multi-channel active noise control system comprising:

loudspeakers arranged relative to a tonal noise source;

at least one microphone for generating at least one error signal positioned at a near field pressure node corresponding to a calculated condition where radiated acoustic power is minimized determined from a model of the tonal noise source and the loudspeakers;

placing a plurality of microphones at locations corresponding to the near field pressure nodes; and an adaptive controller coupled to the loudspeakers and the at least one microphone, wherein the adaptive controller drives each of the loudspeakers with amplitudes and phases selected to minimize tonal noise at the microphone locations.

2. The multi-channel active noise control system according to claim 1, further including a nonacoustic reference sensor for generating a reference signal relating to a tonal noise frequency from the tonal noise source for input to the adaptive controller.

3. The multi-channel active noise control system according to claim 1 wherein the loudspeakers are arranged in an array around the tonal noise source.

4. The multi-channel active noise control system according to claim 1, wherein the loudspeakers comprise an array of loudspeakers around and coplanar with the tonal noise source.

5. The multi-channel active noise control system according to claim 4, wherein each of the loudspeakers in the array is at equal angles around and at equal radii from a center of the tonal noise source.

6. The multi-channel active noise control system according to claim 1, wherein the loudspeakers comprise four loudspeakers.

7. The multi-channel active noise control system according to claim 1, wherein the at least one microphone comprises a plurality of microphones each placed at near-field pressure nodes of a spatial pressure plot corresponding to a condition of minimized acoustic power radiation.

8. The multi-channel active noise control system according to claim 1, wherein the tonal noise source comprises an axial fan generating tonal noise.

9. The multi-channel active noise control system according to claim 8. wherein the tonal noise comprises the radiated acoustic power comprising blade passage frequencies and harmonics thereof.

10. A method of reducing tonal noise emanating from a tonal noise source, comprising:

selectively arranging loudspeakers around the tonal noise source;

calculating near field pressure nodes corresponding to a condition where radiated acoustic power is minimized using a model of the tonal noise source and loudspeakers;

placing a plurality of microphones at locations corresponding to the near field pressure nodes; and driving amplitude and phase of each of the loudspeakers in response to signals generated by the plurality of microphones to minimize tonal noise at the microphone locations.

11. The method according to claim 10, wherein selectively arranging the loudspeakers around the tonal noise source comprises placing each of the loudspeakers coplanar with, and at equal angles and radii around, a center of the tonal noise source.

12. The method according to claim 10, wherein calculating near field pressure nodes comprises:

modeling each of the loudspeakers and the tonal noise source as point source monopoles;

deriving an expression for radiated power based on the modeling;

calculating amplitudes and phases of each of the loudspeakers to minimize the expression for radiated power; and plotting spatial pressure in a plane containing the loudspeakers and the tonal noise source;

determining near-field pressure nodes corresponding to a condition where the radiated power is minimized.

13. The method according to claim 10, further comprising obtaining a frequency associated with the tonal noise emanating from the tonal noise source.

14. The method according to claim 13, wherein the tonal noise source comprises an axial fan.

15. The method according to claim 14, wherein obtaining the frequency associated with the tonal noise comprises using a nonacoustic sensor to measure blade passage frequency and associated harmonics.

16. The method according to claim 10, wherein the tonal noise emanating from the tonal noise source comprises blade passage frequency and associated harmonics emanating from an axial fan.

17. The method according to claim 10, wherein placing a plurality of microphones at locations corresponding to the near field pressure nodes comprises selecting near field pressure nodes located between adjacent speakers.

* * * * *